United States Patent
Whitmore et al.

(10) Patent No.: US 7,563,260 B2
(45) Date of Patent: Jul. 21, 2009

(54) TISSUE WARMING DEVICE AND METHOD

(75) Inventors: Willet F. Whitmore, Sarasota, FL (US);
Winston E. Barzell, Sarasota, FL (US)

(73) Assignee: CIVCO Medical Instruments Co., Inc., Kalona, IA (US)

( * ) Notice: Subject to any disclaimer, the term of this patent is extended or adjusted under 35 U.S.C. 154(b) by 507 days.

(21) Appl. No.: 11/207,716

(22) Filed: Aug. 22, 2005

(65) Prior Publication Data

US 2006/0025709 A1 Feb. 2, 2006

Related U.S. Application Data

(63) Continuation of application No. 10/358,199, filed on Feb. 5, 2003, now Pat. No. 6,932,771, which is a continuation-in-part of application No. 10/190,616, filed on Jul. 9, 2002, now abandoned.

(60) Provisional application No. 60/303,413, filed on Jul. 9, 2001.

(51) Int. Cl.
*A61B 18/02* (2006.01)

(52) U.S. Cl. ............................... 606/21; 606/22; 606/23

(58) Field of Classification Search ............ 607/96, 607/104; 600/439, 459; 606/21, 22
See application file for complete search history.

(56) References Cited

U.S. PATENT DOCUMENTS

| | | | | |
|---|---|---|---|---|
| 4,817,616 A | 4/1989 | Goldstein | ............... | 128/662.06 |
| 5,676,159 A | 10/1997 | Navis | ........................ | 128/846 |
| 5,997,481 A | 12/1999 | Adams et al. | ............... | 600/459 |
| 6,039,694 A | 3/2000 | Larson et al. | ............... | 600/459 |
| 6,126,607 A | 10/2000 | Whitmore, III et al. | ...... | 600/459 |
| 6,267,726 B1 | 7/2001 | Grimm | ....................... | 600/459 |
| 2002/0010502 A1* | 1/2002 | Trachtenberg | ............... | 607/102 |
| 2003/0018256 A1* | 1/2003 | Sasaki et al. | ................ | 600/439 |

* cited by examiner

*Primary Examiner*—Roy D Gibson
(74) *Attorney, Agent, or Firm*—Steptoe & Johnson LLP

(57) ABSTRACT

The present invention relates to a tissue warming device for use with an ultrasound probe having top and bottom sides located diametrically opposite to each other viewed from a frontal cross-section of the probe. The device includes a sheath configured and dimensioned to receive at least a portion of the probe. A first sack, which is associated with the sheath, covers at least a portion of the top side of the probe. The sack includes first and second passages. The first passage allows warm fluid to be directed into the first sack for expansion thereof. The second passage allows fluid to be removed from the first sack. When expanded with warm fluid, the first sack warms body tissue disposed adjacent thereto. The warm fluid may be a warm liquid, such as an aqueous liquid.

23 Claims, 5 Drawing Sheets

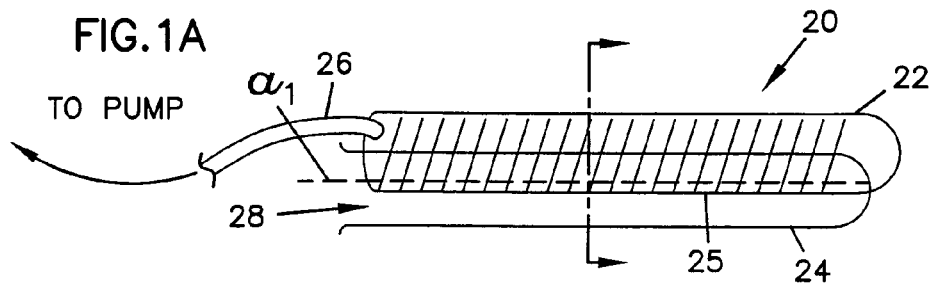
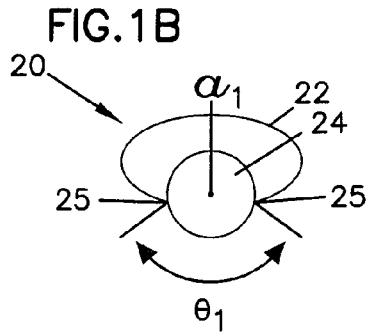
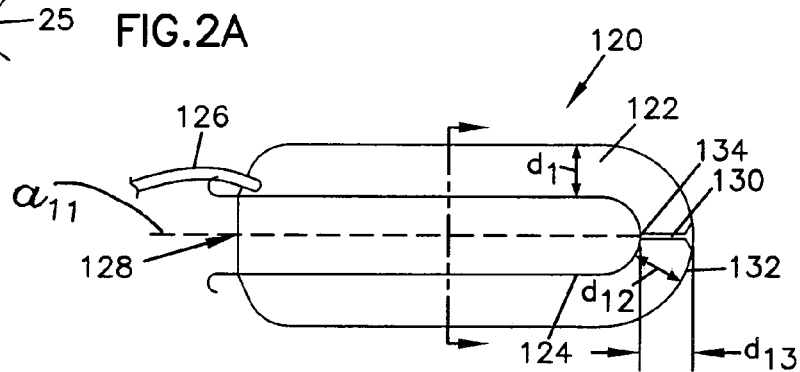
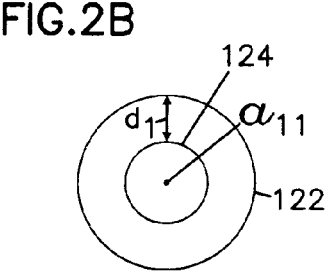
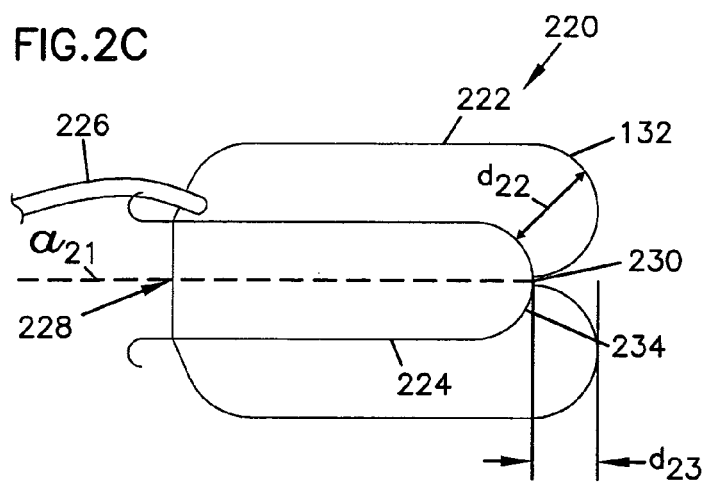

TISSUE WARMING DEVICE AND METHOD

RELATED APPLICATIONS

The present application is a continuation of application Ser. No. 10/358,199 filed Feb. 5, 2003, now U.S. Pat. No. 6,932,771 which is a continuation-in-part of application Ser. No. 10/190,616, filed Jul. 9, 2002 now abandoned, and claims the benefit of provisional application Ser. No. 60/303,413, filed Jul. 9, 2001, which applications are incorporated herein by reference thereto.

FIELD OF THE INVENTION

The present invention relates to a tissue warming and/or cooling device and method, and in particular, to a tissue warming device and method for warming the rectum to prevent injury during cryotherapy treatment of the prostrate.

BACKGROUND OF THE INVENTION

Cryotherapy is a promising treatment for many conditions. For example, cryosurgery has been used for many years in the treatment of skin cancers. This technology is now being utilized in the treatment of cancers of the liver, prostate, pancreas, and kidney. Although cryotherapy for treatment of prostate cancer dates back to-the 1960's, the high rate of complications, such as inadvertent freezing of the rectum which created rectal fistulas between the prostate, the rectum, and the urethra, limited the widespread application of this treatment for many years.

Advances in transrectal ultrasound, the development of computerized instrumentation to control the freezing probes, and the development of wires and tubes have enabled precise cryosurgery leading to renewed interest in cryotherapy treatment of prostate cancer. For example, the border of the freezing zone created during cryotherapy is visible by ultrasound so that the ice ball created in the prostate by the freezing can be seen.

Cryotherapy of the prostate is performed with the patient in the lithotomy position, using an ultrasound imaging probe placed in the rectum to guide an instrument called a cryoprobe and to monitor the freezing of the prostate. Typically, in cryotherapy, liquid nitrogen or a similar freezing agent is circulated through the cryoprobe, which is placed in contact with the tumor. The tumor is frozen as is some of the surrounding tissue. Often, the treatments are cyclic in which the tumor is frozen, allowed to thaw, and then refrozen. The goal of this treatment is to rapidly kill the cancer cells without subjecting the surrounding healthy tissue to trauma.

In order to optimize the cryotherapy treatment, the ultrasound images should accurately reflect the anatomy. A stable liquid interface covering the transducers on the ultrasound probe improves image quality. The present invention is directed to a tissue warming and/or apparatus and method that can be used with these ultrasound transducer covers.

SUMMARY OF THE INVENTION

A first aspect of the invention relates to a device for use with an ultrasound probe having an ultrasound emitter. In one embodiment, the device comprises a sleeve configured and dimensioned to receive at least a portion of the probe therein, a sheath operatively associated with the sleeve, the sheath and the sleeve defining a first substantially enclosed volume therebetween, wherein when the probe is received within the sleeve, the first substantially enclosed volume covers at least a portion of the ultrasound emitter, a first passage comprising a first opening fluidically associated with the first substantially enclosed volume for introducing a warm or cool liquid into the first substantially enclosed volume for expansion thereof and to warm or cool body tissue adjacent the first substantially enclosed volume, and a second passage having a second opening fluidically associated with the first substantially enclosed volume for removing liquid therefrom.

The first and second openings may be the same opening or may be spaced apart from one another.

The device may further comprise a first pump to provide a flow of liquid into the first substantially enclosed volume through the first passage and a flow of liquid out of the first substantially enclosed volume through the second passage. The device may comprise a liquid heater configurable to heat the liquid to a temperature of at least 33° C., for example, at least 37° C., for example, at least 40° C. The device may comprise a liquid cooler configurable to cool the liquid to a temperature of less than 37° C., for example, less than 10° C.

The device may comprise a second pump that cooperates with the first pump to provide the flow of warm or cool liquid into the first substantially enclosed volume and the flow of liquid out of the first substantially enclosed volume.

The device may further comprise a second substantially enclosed volume, which may be expandable independently of the first substantially enclosed volume. The second substantially enclosed volume may be expandable and surround at least a portion of the first sheath. Expansion of the first substantially enclosed volume may form a first interface and expansion of the second substantially enclosed volume may form a second, different interface.

Another aspect of the invention relates to a device for forming a liquid interface between an ultrasound probe and tissue of a mammal. The device may comprise an inner sheath having a longitudinal axis, the inner sheath being configured to receive therein at least a portion of an ultrasound probe along the longitudinal axis, an outer sheath enveloping at least a portion of the inner sheath, wherein the outer sheath and the portion of the inner sheath enveloped by the outer sheath form a substantially enclosed volume therebetween, the substantially enclosed volume having first and second portions, an at least substantially circumferential first junction joining the inner and outer sheaths, wherein the first portion of the substantially enclosed volume is disposed proximal to the first junction and the second portion of the substantially enclosed volume is disposed distal to the first junction a liquid source for introducing liquid to the substantially enclosed volume, and a passage fluidically connecting the first and second portions of the substantially enclosed volume, through which passage fluid in one of the first and second portions of the substantially enclosed volume may pass to the other of the first and second portions of the substantially enclosed volume.

Yet another aspect of the invention relates to a device for forming a liquid interface between an ultrasound probe and tissue of a mammal, the ultrasound probe having a distal end. The device may comprise a distal tip, an inner sheath having a longitudinal axis, the inner sheath being configured to receive therein at least a portion of an ultrasound probe along the longitudinal axis, an outer sheath enveloping at least a portion of the inner sheath, wherein the outer sheath and the portion of the inner sheath enveloped by the outer sheath form a substantially enclosed volume therebetween, and wherein a distal end of the distal tip extends distally beyond the outer sheath along the longitudinal axis. The distal tip may comprise a proximal portion configured to abut the distal end of the ultrasound probe.

In another embodiment, the device may comprise an inner sheath having a longitudinal axis, the inner sheath being configured to receive therein at least a portion of an ultrasound probe along the longitudinal axis, an outer sheath enveloping at least a portion of the inner sheath, wherein the outer sheath and the portion of the inner sheath enveloped by the outer sheath form a substantially enclosed volume therebetween, and a distal tip configured to abut the distal end of the ultrasound probe along the longitudinal axis of the inner sheath.

In another embodiment, the device may comprise a distal tip, an inner sheath having a longitudinal axis, the inner sheath being configured to receive therein at least a portion of an ultrasound probe along the longitudinal axis, an outer sheath enveloping at least a portion of the inner sheath, wherein the outer sheath and the portion of the inner sheath enveloped by the outer sheath form a substantially enclosed volume therebetween, and wherein a distal portion of the outer sheath is secured to a circumference of the distal tip.

In yet another embodiment, the device may comprise a distal tip, an inner sheath having a longitudinal axis, the inner sheath being configured to receive therein at least a portion of an ultrasound probe along the longitudinal axis, an outer sheath enveloping at least a portion of the inner sheath, wherein the outer sheath and the portion of the inner sheath enveloped by the outer sheath form a substantially enclosed volume therebetween, and wherein a distal portion of the outer sheath is secured to a circumference of the distal tip. The circumference of the distal tip may be circular. The circumference of the distal tip may have a diameter of at least 14 mm.

In an additional embodiment, the device may comprise a distal tip, an inner sheath having a longitudinal axis, the inner sheath being configured to receive therein at least a portion of an ultrasound probe along the longitudinal axis, an outer sheath enveloping at least a portion of the inner sheath, wherein the outer sheath and the portion of the inner sheath enveloped by the outer sheath form a substantially enclosed volume therebetween, and wherein a distal portion of at least one of the inner and outer sheaths is secured to the distal tip and wherein a portion of the distal tip proximal to the secured distal portion of the at least one inner or outer sheath has a radial dimension of at least 14 mm.

BRIEF DESCRIPTION OF THE DRAWINGS

The present invention is discussed below in reference to the drawings in which:

FIG. 1a shows a first embodiment of a device in accordance with the present invention, the device being shown in the expanded state;

FIG. 1b shows a cross-sectional view of the device of FIG. 1a;

FIG. 2a shows a second embodiment of a device in accordance with the present invention;

FIG. 2b shows a cross-sectional view of the device of FIG. 2a;

FIG. 2c shows a third embodiment of a device in accordance with the present invention;

FIG. 5b shows a cross-sectional view of the device of FIG. 5a;

DESCRIPTION OF THE PRESENT INVENTION

Figure 3A:
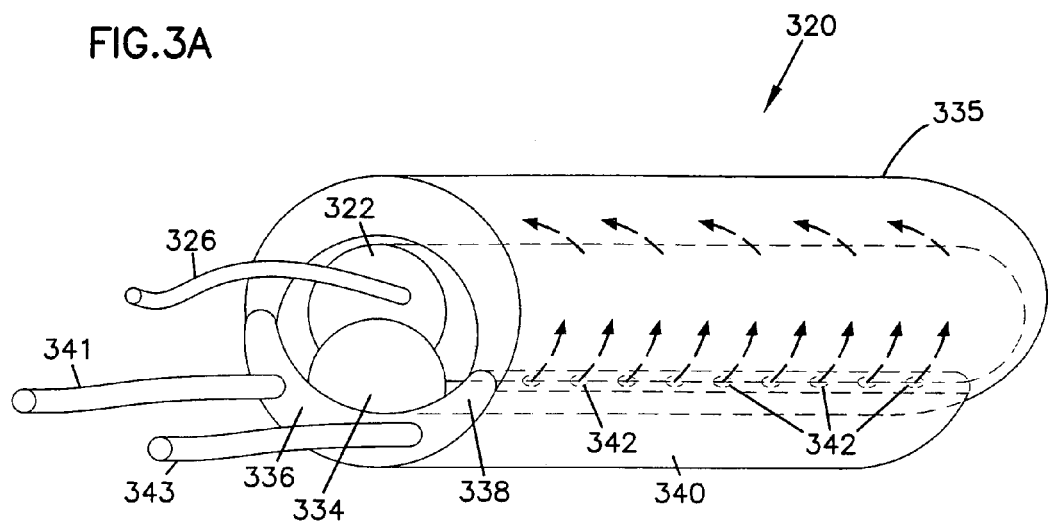
FIG. 3a shows a fourth embodiment of a device in accordance with the present invention.
Figure 3B:
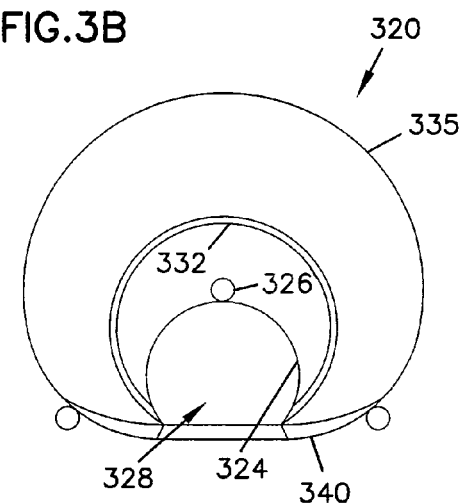
FIG. 3b shows a cross-sectional view of the device of FIG. 3a, an outer thermal sleeve of the device being shown in the expanded state.
Figure 3C:
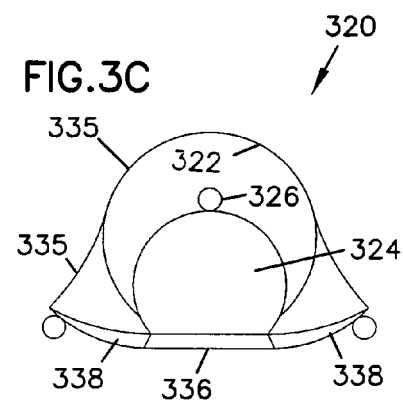
FIG. 3c shows the cross-sectional view of FIG. 3b, an outer-thermal sleeve of the device being shown in the non-expanded state.
Figure 3D:
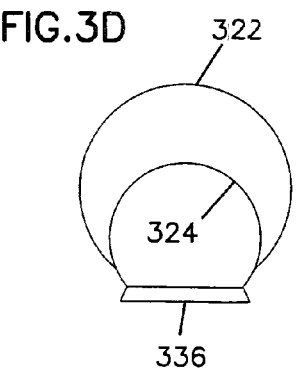
FIG. 3d shows the device of FIG. 3a, the outer thermal sheath being removed.

One aspect of the present invention relates to a device that may be used to warm and/or cool tissue, such as tissue of a mammal. In one embodiment, the device is configured for use with an ultrasound probe to provide a fluid interface between an ultrasound emitter of the ultrasound probe and tissue of a mammal. The fluid is preferably a liquid, such as water or saline solution. The device provides a sheath configured and dimensioned to receive at least a portion of the probe. A first substantially enclosed volume covers at least a portion of the top side of the probe. A first passage is associated with the first substantially enclosed volume for directing a warm fluid therein to expand the substantially enclosed volume. The first substantially enclosed volume, when expanded with warm fluid, is configured to warm body tissue disposed adjacent an outer surface of the substantially enclosed volume. The first substantially enclosed volume may be expanded with cool liquid to cool adjacent body tissue. The first substantially enclosed volume includes a second passage for removing fluid therefrom. In a preferred embodiment, the device includes the ultrasound probe.

Referring to FIGS. 1a and 1b, a device 20 for use with an ultrasound probe, such as a transrectal ultrasound transducer includes an expandable sheath 22 and an inner sleeve 24. An ultrasound probe, not shown, may be introduced along a longitudinal axis a, of inner sleeve 24 via an opening 28 of the inner sleeve. Expandable sheath 22 may be secured to inner sleeve 24, such as along a seam 25. Seam 25 may be formed, for example, of adhesive or by ultrasonic welding.

Expandable sheath 22 may be expanded by introducing liquid therein via a liquid source 26, which may comprise tubing or like structure that provides a passage for liquid. Liquid source 26 may cooperate with a liquid drain to allow fluid to exit expandable sheath 22. For example, the liquid drain may be liquid source 26 through which liquid exits expandable sheath 22. Liquid source 26 may include at least two lumina. Liquid may be introduced to expandable sheath 22 along at least a first one of the lumina. Liquid may exit the expandable sheath along at least a second, optionally different, one of the lumina. Of course, the at least two lumina may be configured as different tubes rather than a single tube with a plurality of lumen. Where different tubes are used, the inflow and outflow tubing ends may be located at spaced apart locations of the expandable sheath to improve the distribution and mixing of liquid within the sack.

Upon expansion with a liquid and insertion into a portion of an animal, such as the rectum of the animal, expandable sheath 22 provides a liquid interface between an ultrasound probe residing within inner sleeve 24 and tissue of the animal adjacent the outer surface of expanded expandable sheath 22. Preferably, ultrasound radiation emitted from the ultrasound probe may propagate through the expandable sheath 22 before striking the tissue. Ultrasound radiation reflected from the tissue may propagate back through the expanded sack 22 before being received by the ultrasound probe. As seen in FIG. 1b, expandable sheath 22 allows such emission and reception of ultrasound radiation over an angle of $360°-\theta_1$, where $\theta_1$ is an angle of less than 180°, for example less than 120°, such as less than 90°.

Device 20 may include a pump to provide a flow of liquid into the expandable sheath 122 through the liquid source 126. The temperature of the liquid may be determined using a thermostat. In one embodiment, the liquid may have a temperature of at least 33° C., for example, at least 37° C., at least 40° C., or even at least 45° C. Alternatively, the temperature of the liquid may be less than 37° C., for example, less than 30° C., less than 20° C., less than 10° C., less than 5° C., or 0° C. or less than 0° C. Liquid having these temperatures may be used with any embodiment of a device of the present invention.

One method for introducing liquid to devices of the invention comprises manual introduction. For example, the device may include a liquid source comprising a single lumen. The expandable sheath may be filled with liquid to a useful capacity, for example, from about 10 to about 15 cc of liquid. During use, liquid may be introduced or withdrawn to further expand or contract the expandable sheath as necessary to provide an ultrasound interface or maintain a desired interface temperature. During withdrawal of liquid, a user must accept any minor changes in the ultrasound image that could occur with the varying thickness of the interface between the patient's anatomy and the ultrasound transducer resulting from the volume changes in the expandable sheath with each cycle of filling and partial emptying. A liquid source comprising double lumina may also be used for manually introducing and withdrawing fluid from the expandable sheath.

Liquid may also be introduced and withdrawn from a device of the invention using one or more pumps. For example, a single pump operating at constant pressure may be used to introduce liquid to expandable sheath 22. A flow restriction on a liquid drain from the expandable sheath could be used to limit the rate at which fluid exits the expandable sheath. The flow restriction may be variable to allow different flow rates of liquid through the expandable sheath. The resulting volume of the expandable sheath is determined by the pressure volume relationship of the expandable sheath, which relationship is readily determined either empirically or based upon the construction and material properties of the device. Preferably, the device is expanded with fluid to provide desired imaging characteristics. A single recirculating pump operating with this constant volume circulates the fluid. Thus, the preferred system is a closed recirculating system. A heat exchanger to warm or cool the circulating fluid may be included. Thus, a predetermined temperature of the liquid that circulates through the expanded sheath may be used to warm or cool adjacent tissues.

In another embodiment of the invention a first pump determines the amount of fluid introduced to the device and a second pump determines the amount of fluid exiting the device. Preferably, both pumps are metering pumps that deliver a predetermined volume rate of liquid. The temperature of liquid introduced to and exiting from the expandable sheath may be monitored to determine the progress of thermal therapies. For example, during cryotherapy of the prostate, warm liquid may be introduced to the expandable sheath of a device of the invention. As cryotherapy proceeds, tissue adjacent the rectum begins to cool. Heat from liquid circulating through the expandable sheath is transferred to the cooled tissue thereby cooling the liquid. By monitoring the temperature drop of the liquid, the progress of the cryotherapy may be determined. Thus, the cryotherapy may be stopped or paused before the cryotherapy induced ice ball damages rectal tissue.

Referring to FIGS. 2a-2b, a device 120 includes an expandable sheath 122, which completely surrounds a radial dimension of an inner sleeve 124. An ultrasound probe (not shown) may be introduced within inner sleeve 124 along a longitudinal axis $a_{11}$ thereof. Expandable sheath 122 may be expanded by introducing liquid therein. A liquid source 126, which may be identical with liquid source 126, may be used to introduce liquid to and allow liquid to exit from expandable sheath 122. Upon expansion with a liquid and insertion into a portion of an animal, expandable sheath 122 provides a liquid interface between an ultrasound probe residing within inner sleeve 124 and tissue of the animal adjacent the expanded expandable sheath 122, as discussed above for device 20.

Device 20 preferably includes a distal tip 130 configured to maintain a position of an ultrasound transducer residing within inner sleeve 124 with respect to expandable sheath 122. Distal tip 130 preferably joins an outer wall 132 of expandable sheath 122 with a distal portion 134 of inner sleeve 122. By joining outer wall 132 and inner sleeve 124, distal tip 130 preferably inhibits movement of outer wall 132 with respect to inner sleeve 124 thereby maintaining a substantially constant radial distance $d_1$ between inner sleeve 124 and outer wall 132. Device 120, therefore, provides a stable interface between an ultrasound emitter of an ultrasound probe inserted within inner sleeve 124 and tissue of an animal.

Referring to FIG. 2c, a device 220 includes a distal tip 230 joining an outer wall 232 of an expandable sheath 222 and a distal portion 234 an inner sleeve 224. Distal tip 230 serves the same function as distal tip 130 of device 120. An ultrasound probe (not shown) may be introduced within inner sleeve 224 along a longitudinal axis $a_{21}$ thereof. A liquid source 226 may be identical with liquid source 26 of device 20. The embodiment of FIG. 2c has a cross-section that may be identical with the cross-section of device 120 shown in FIG. 2b.

Referring back to FIG. 2a, a radial distance $d_{12}$ at distal tip 130 between outer wall 132 of expandable sheath 122 and inner sleeve 124 may be substantially identical with a radial distance $d_{13}$ adjacent distal tip 130 between outer wall 132 of expandable sheath 122 and inner sleeve 124. Returning to FIG. 2b, a radial distance $d_{22}$ at distal tip 130 between outer wall 132 of expandable sheath 122 and inner sleeve 124 may be substantially identical with a radial distance $d_{23}$ at distal tip 130 between outer wall 132 of expandable sheath 122 and inner sleeve 124.

Referring to FIGS. 3a-3d, a device 320 includes a thermal envelope 335 that is distinct from an expandable sheath 322, which thermal envelope provides a stable liquid interface for transmission and reception of ultrasound energy as described above. Liquid may be introduced to expandable sheath 322 via a liquid source 326, which may be identical with liquid source 26 discussed above.

A base 333 of device 320 includes a first portion 336 adapted to secure the ultrasound probe when received within an inner sleeve 324 via an opening 328. Second portions 338 of base 333 are configured to facilitate attachment of the thermal envelope 335. An outer surface 340 of base 333 is formed to be "anatomically friendly" with smooth features and finish. Liquid may be introduced to thermal envelope 335 via a liquid source 343. A liquid drain 341 may be provided to allow liquid to drain from thermal envelope 335. Preferably, liquid having a predetermined temperature circulates into, through, and out of thermal envelope 335, thereby maintaining a substantially constant temperature thereof. A second portion 338 of base 333 may include ports 342 through which liquid from liquid source 343 is introduced to thermal envelope 335. Substantially identical ports on an opposed second portion 338 may drain fluid from thermal envelope 335 to liquid drain 341.

The thermal envelope 335 may be either manually or automatically filled with warming liquid to maintain a predetermined temperature range in contact with a patient's anatomy. Expandable sheath 322 may be used to position and or shape the anatomy of interest with respect to the ultrasound probe as well as providing improved ultrasound transmission and reception. In use, the volume of expandable sheath 322 and thermal envelope 325 is determined by the amount of fluid introduced thereto. A user may vary the amount of fluid introduced until desired ultrasound image characteristics and thermal characteristics are achieved. Thermal envelope 335, expandable sheath 322, and inner sleeve 324 may comprise thin sheets of material. Each sheet may have different strength, temperature, and sono-lucent characteristics.

Figure 4:
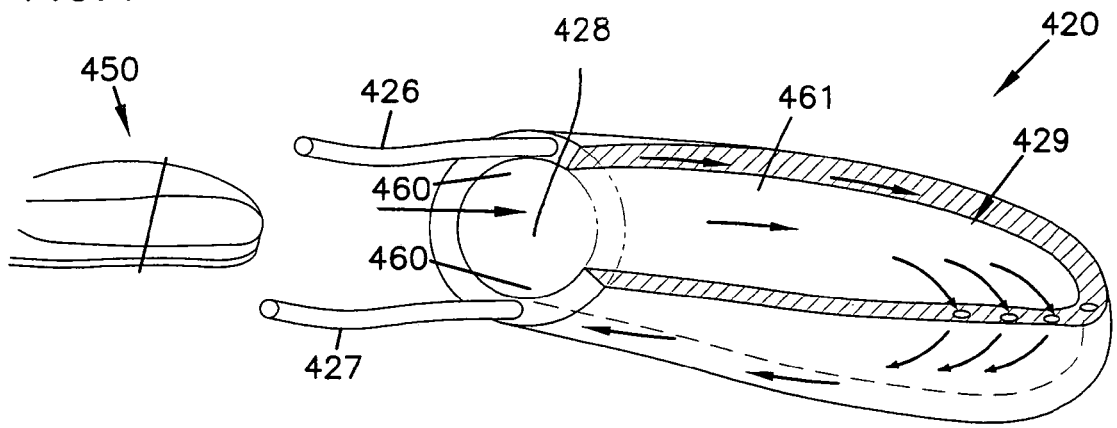
FIG. 4 shows a fifth embodiment of a device in accordance with the present invention.

Referring to FIG. 4, a device 420 may be used in conjunction with currently available devices for providing a liquid interface adjacent an ultrasonic probe. Suitable ultrasonic probes are disclosed in U.S. Pat. No. 6,126,607, which is incorporated herein by reference. In use, an ultrasonic probe 450 associated with an envelope for providing a liquid interface is received along a longitudinal axis of device 420 via an opening 428. An inner layer 460 and an outer layer 461 of device 420 form a substantially enclosed volume 429 therebetween. Liquid is introduced to the enclosed volume 429 of device 420. Liquid may exit device 420 via a liquid drain 427.

Figure 5A:
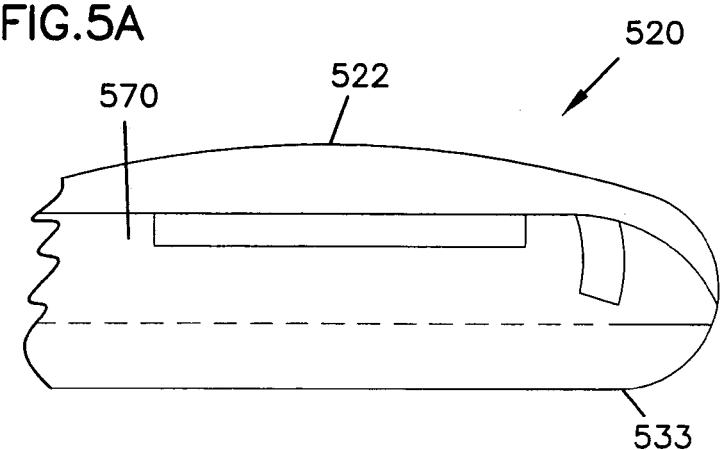
FIG. 5a shows a sixth embodiment of a device in accordance with the present invention.
Figure 5B:
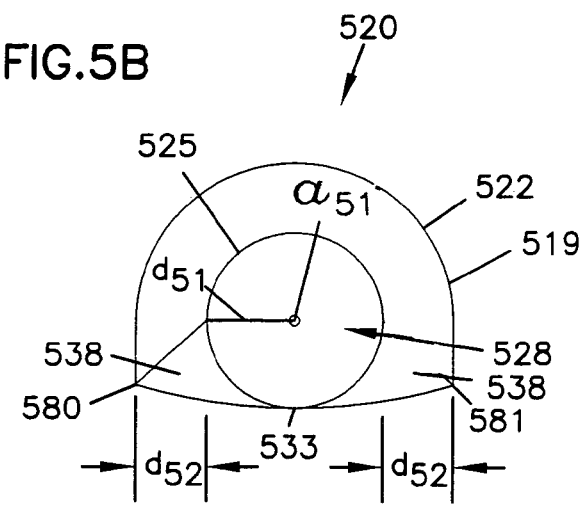
Figure 6A:
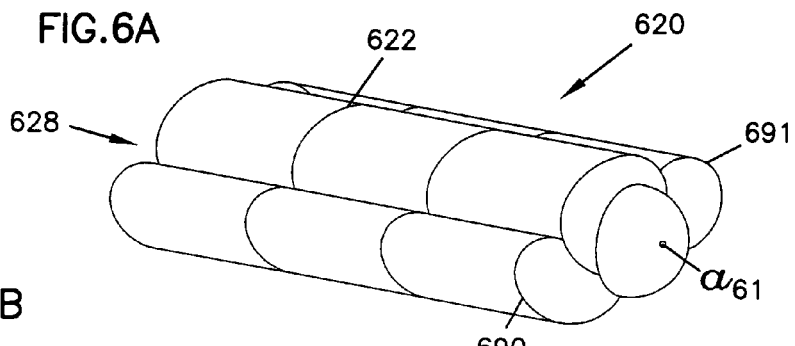
FIG. 6a shows a seventh embodiment of a device in accordance with the present invention, the device being in an expanded state.
Figure 6B:
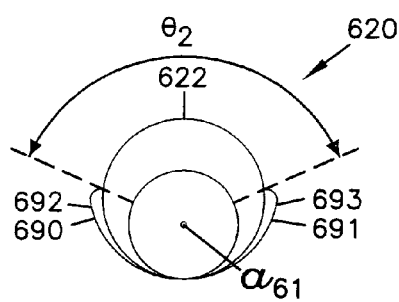
FIG. 6b shows a cross-sectional view of the device of FIG. 6a, the device being in a non-expanded state.
Figure 6C:
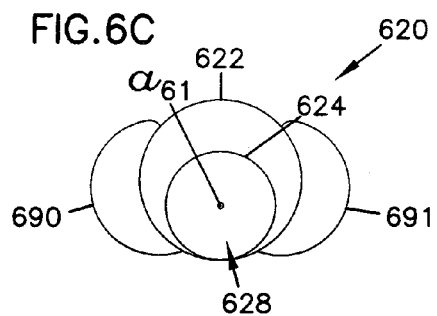
FIG. 6c shows a cross-sectional view of the device of FIG. 6a, the device being in an expanded state.
Figure 6D:
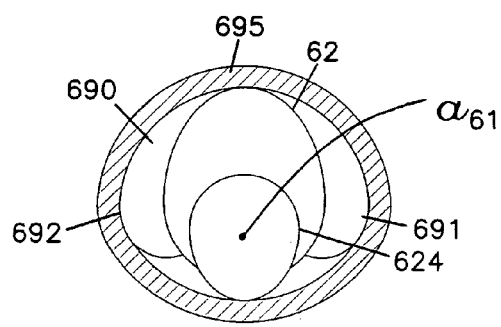
FIG. 6d shows a cross-sectional view of the device of FIG. 6a disposed within the anatomy of a mammal, the device being in an expanded state.

Referring to FIGS. 5a and 5b, a device 520 includes an expandable sheath 522 and an inner sleeve 524 having an opening 528 to receive an ultrasound probe 570 therein. Inner sleeve 524 has a radial dimension $d_{51}$. A base 533 includes portions 538 that extend a further radially by a distance $d_{52}$ than inner sleeve 524. Portions 538 also radially extend lower, outer edges 580, 581 of expandable sheath 522 by distance $d_{52}$ beyond inner sleeve 524. Because edges 580, 581 of expandable sheath 522 are radially extended, an outer surface 519 of expandable sheath 522 presents a greater surface area for contacting the anatomy of a patient. Expandable sheath 522 may be filled with liquid having a predetermined temperature, such as warmer or cooler than a patient's tissue. The greater surface area presented by outer surface 519 efficiently warms or cools the anatomy.

Referring to FIGS. 6a-6d, a device 620 includes an expandable sheath 622 and an inner sleeve 624 identical with expandable sheath 22 and inner sleeve 24 of device 20. Device 620, however, includes lateral sacks 690, 691, which may be expanded, such as by the introduction of liquid thereto, independently of expandable sheath 622. Outer surfaces 692, 693 of lateral sacks 690, 691 provide increased contact area with a patient's anatomy 695. Liquid having a predetermined temperature may be introduced into lateral sacks 690, 691.

Lateral sacks 690, 691 preferably provide an angular viewing range $\theta_{61}$ for ultrasound imaging of at least 90° when non expanded. When device 620 is present in the anatomy, lateral sacks 690, 691 may be returned to the non-expanded state, such as be removing liquid therefrom, thereby increasing the angular viewing range. Because lateral sacks 690, 691 expand independently of expandable sheath 622, device 620 maintains a liquid interface between an ultrasound probe received therein and a patient's anatomy whether the lateral sacks are expanded or not.

Figure 7:
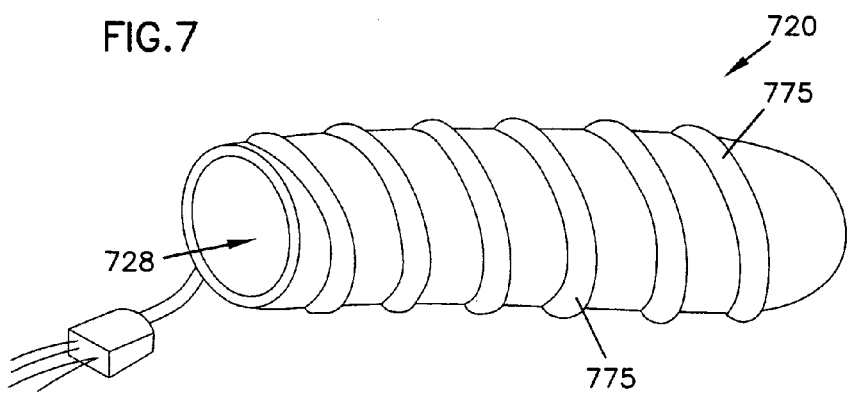
FIG. 7 shows an eighth embodiment of a device in accordance with the present invention.

Referring to FIG. 7, a device 720 receives an ultrasound probe via an opening 728 thereof. Device 720 includes a resistive element 775 through which a low voltage, current may be introduced to create an increased temperature adjacent a patient's anatomy during, for example, cryosurgery or cryotherapy. Device 720 may be comprised of a formed plastic or rubber sleeve.

Figure 8A:
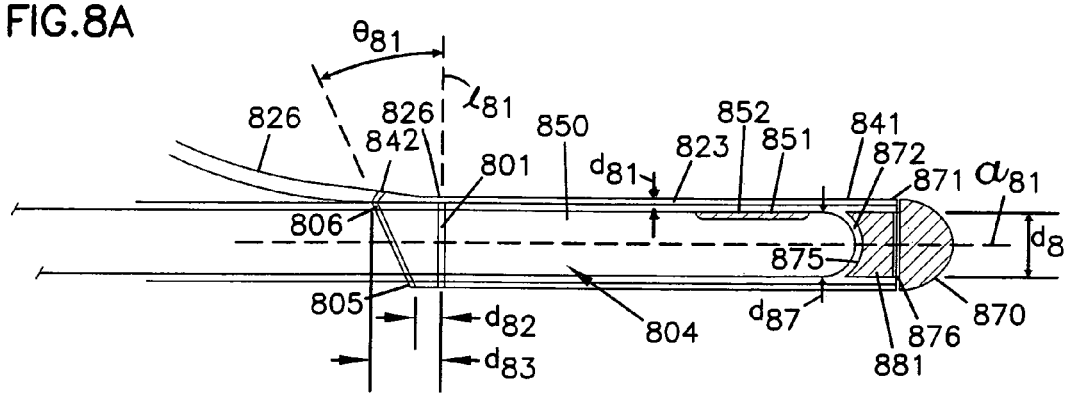
FIG. 8a shows a ninth embodiment of a device in accordance with the present invention, the device being in a non-expanded state.
Figure 8B:
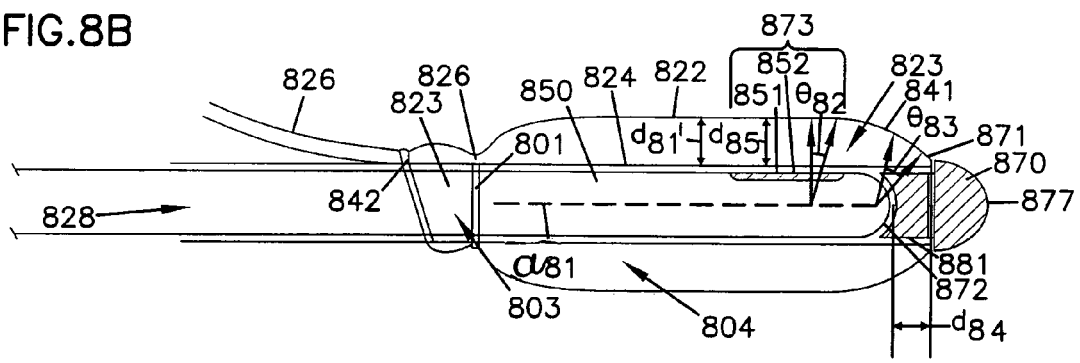
FIG. 8b shows the device of FIG. 8a, the device being in an expanded state.

Referring to FIGS. 8a and 8b, a device 820 of the invention is configured to provide a liquid interface between an ultrasound probe 850 and tissue of a mammal. At least a portion of the ultrasound probe 850 is received within an inner sleeve formed by an inner sheath 824 along a longitudinal axis $a_{81}$ of the sleeve. A preferably expandable outer sheath 822 envelopes at least a portion of the inner sheath 824 forming a substantially enclosed volume 823 therebetween. By substantially enclosed, it is meant that liquid may be introduced to substantially enclosed volume 823 to increase a radial dimension d81 volume 823 in a non-expanded state (FIG. 8a) to a greater radial dimension d81' in an expanded state (FIG. 8b). In the expanded state, substantially enclosed volume provides a liquid interface for transmitting ultrasound energy from ultrasound emitters 851 of ultrasound probe 850 and receiving ultrasound energy reflected from tissue of a patient's anatomy by ultrasound receivers 852.

An at least substantially circumferential first junction 801 joins the inner and outer sheaths 824, 822. A first portion 803 of the substantially enclosed volume 823 is disposed proximal to the first junction 801 and a second portion 804 of the substantially enclosed volume 823 is disposed distal to the first junction 801. By at least substantially circumferential, it is meant-that the first junction 801 joins at least 50%, for example, at least 75%, or at least 90% of the circumference of outer sheath 522 and inner sheath 524. Although the term circumference is used, the periphery of outer sheath 522 and inner sheath 524 may be any shape including non-circular shapes.

A passage 876 fluidically connects the first and second portions 803, 804 of the substantially enclosed volume 823. Liquid or gas in one of the first and second portions of the substantially enclosed volume may pass across first junction to the other of the first and second portions of the substantially enclosed volume. For example, gas present in second portion 804 may pass through passage 876 to first portion 803, thereby preventing the gas, in the form of bubbles, from interfering with transmission or reception of ultrasound radiation.

A liquid source 826 may be used for introducing liquid to the substantially enclosed volume. Liquid source 826 may be configured to introduce liquid into the second portion 804 of substantially enclosed volume 823. Preferably, liquid source 826 extends to a distal portion 841 of substantially enclosed volume 823. A liquid drain may be provided to allow liquid to exit the substantially enclosed volume. For example, as discussed above with respect to liquid source 26 of device 20, liquid source 826 may include multiple lumina by at least one of which liquid may be introduced and by at least one of which liquid may exit or be withdrawn. Alternatively, the liquid drain may comprise a tube separate from liquid source 826.

The liquid drain may be configured to remove liquid from the first portion 803. In one embodiment, liquid is introduced at distal portion 841 substantially enclosed volume 823 flows proximally through volume 823 and exits via a liquid drain at a proximal portion 842 of volume 823. Liquid introduced into the second portion of the substantially enclosed volume may pass through passage 826 to the first portion 803 of the substantially enclosed volume 823. In any event, the liquid drain is preferably configured to remove liquid from the first portion of the substantially enclosed volume.

Device 820 may include a second at least substantially circumferential junction 802 joining the inner and outer sheaths. The second junction 802 preferably includes a first point 805 disposed at a first axial distance $d_{82}$ from the first junction 801 and a second point 806 disposed at a second, greater axial distance $d_{83}$ from the first junction 801. The liquid drain is preferably disposed closer to second point 806 than first point 805. The second junction 802 may be disposed at an angle $\theta_{81}$ with respect to a line $l_{81}$ normal to the longitudinal axis $a_{81}$. Second junction 801 is preferably parallel with line $l_{81}$. Angle $\theta_{81}$ is preferably at least 5°, for example at least 15°, or at least 20°.

Device 820 includes a distal tip 870 preferably configured to extend a distal portion 871 of at least outer sheath 822 distally by a distance $d_{84}$ beyond a distal end 872 of ultrasound probe 850. Extending distal portion 871 distally is advantageous for at least two reasons. First, ultrasound radiation transmitted and received by ultrasound emitter 851 and receiver 852 propagate through a portion 873 of outer sheath 822 having a larger radius of curvature compared to a radius of curvature of distal portion 871. Referring to FIG. 8b, the radius of curvature of portion 873 is defined for a perimeter lying in the plane of FIG. 8b as shown by angle $\theta_{82}$ and the radius of curvature of portion 871 is defined for a perimeter lying in the plane of FIG. 8b as shown by angle $\theta_{83}$. Because of the increased radius of curvature, ultrasound radiation propagates a more uniform radial distance $d_{85}$ through the enclosed volume 823 than would ultrasound radiation propagating closer to distal portion 871. A second advantage is that distal portion 871 of outer sheath 822 may include non-uniformities, such as wrinkles in the outer surface. In the present embodiment, these non-uniformities are moved distally away from the ultrasound emitter and receiver of the probe.

Distal tip 870 may include a proximal surface 875 that abuts distal end 872 of ultrasound probe 850. Proximal surface 875, may be configured to have a complementary shape to distal end 872 to enhance stability of the device with respect to the ultrasound probe therein. Distal tip 870 preferably includes a distal end 877 that extends beyond distal portion 871 of outer sheath 822.

Outer sheath 822 and, preferably, inner sheath 824 may be secured to distal tip 870. The securement may be mechanical, for example by pinching distal portions of the inner and outer sheaths within a portion 876 of distal tip 870. Alternatively, adhesive or ultrasonic welding may be used to secure the outer sheath and inner sheath to the distal tip. The securement is preferably circumferential. For example, distal portion 871 of outer sheath 822 may be secured to a circumference of the distal tip 870. A second proximal portion 881 of distal tip 870 is preferably disposed proximal to the portion of outer sheath 822 secured to the distal tip. Second proximal portion 881 preferably has a radial dimension $d_{86}$ that is at least 75%, for example, at least 85%, such as at least 90%, of a radial dimension $d_{87}$ of a distal end of an ultrasound probe used with device 820. In a referred embodiment, the proximal portion 881 has a radial dimension $d_{86}$ of at least 14 mm, such as at least 16 mm, for example, at least 18 mm.

Figure 9:
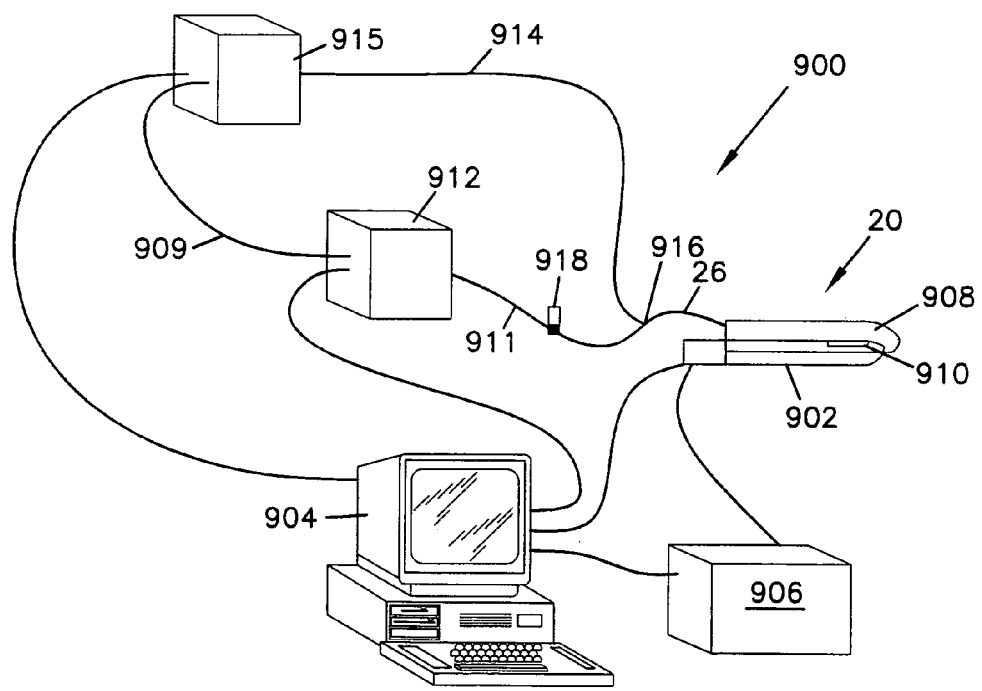
FIG. 9 shows an ultrasound system of the present invention.

Referring to FIG. 9, an exemplary ultrasound system 900 for use with a device of the invention is shown. System 900 includes an ultrasound probe 902, such as a probe for transrectal imaging. The ultrasound probe 902 may be operated using a processing unit, such as a computer 904 and an ultrasound power supply 906. Ultrasound data is received from ultrasound probe 902 and viewed suing computer 904.

In use, a device of the invention, such as, for example, device 20, is provides a preferably liquid-filled interface 908 through which ultrasound is emitted and received by an ultrasound transducer 910 of the ultrasound probe 902. Device 20 may include a fluid circulating unit 912 that preferably includes at least one pump for flowing liquid through interface 908. Fluid circulating unit 912 preferably includes at least one of a liquid heating unit for heating the liquid and a liquid cooling unit for cooling the liquid. Fluid circulating unit 912 may be operated using a computer, such as computer 904. The fluid circulating unit may be independent of the units for heating and cooling, if present.

The liquid heater is preferably configurable to heat the liquid to a temperature of at least 33° C., or at least 37° C., for example, at least 40° C. The liquid cooler is preferably configurable to cool the liquid to a temperature of less than 37° C., for example, less than 10° C.

While various descriptions of the present invention are described above, it should be understood that the various features can be used singly or in any combination thereof. Therefore, this invention is not to be limited to only the specifically preferred embodiments depicted herein. Further, it should be understood that variations and modifications within the spirit and scope of the invention may occur to those skilled in the art to which the invention pertains. Accordingly, all expedient modifications readily attainable by one versed in the art from the disclosure set forth herein that are within the scope and spirit of the present invention are to be included as further embodiments of the present invention.

What is claimed is:

1. A method of performing cryotherapy of a prostate, the method comprising:
   forming a substantially enclosed liquid interface between the prostate and an ultrasound transducer; and
   delivering a freezing agent proximate the prostate to freeze tissue thereof;
   wherein the substantially enclosed liquid interface comprises at least one expandable enclosure.

2. The method of claim 1, further comprising:
   regulating temperature of liquid of the substantially enclosed liquid interface.

3. The method of claim 2, wherein the temperature is at least 33 ° C.

4. The method of claim 2, wherein the temperature is less than 37 ° C.

5. The method of claim 2, wherein the liquid is water or saline solution.

6. The method of claim 1, further comprising:
   heating liquid of the substantially enclosed liquid interface using a liquid heater.

7. The method of claim 1, further comprising:
   cooling liquid of the substantially enclosed liquid interface using a liquid cooler.

8. The method of claim 1, further comprising:

circulating liquid of the substantially enclosed liquid interface.

9. The method of claim 1, further comprising:

recirculating liquid of the substantially enclosed liquid interface in a closed loop.

10. The method of claim 1, further comprising:

monitoring temperature of liquid of the substantially enclosed liquid interface and stopping cryotherapy as a function of the temperature of the liquid.

11. The method of claim 1, wherein the substantially enclosed liquid interface comprises first and second expandable enclosures.

12. The method of claim 1, further comprising:

imaging the prostate using the ultrasound transducer.

13. The method of claim 12, further comprising:

monitoring a freezing zone with the imaging as tissue of the prostate is frozen.

14. A method of performing cryotherapy of a prostate, the method comprising;

forming a substantially enclosed volume of liquid between the prostate and a transrectal imaging probe; and delivering a freezing agent proximate the prostate to freeze tissue thereof;

wherein the substantially enclosed volume of liquid comprises at least one expandable enclosure with liquid therein.

15. The method of claim 14, further comprising:

regulating temperature of liquid of the substantially enclosed volume of liquid.

16. The method of claim 14, further comprising:

pumping liquid into the substantially enclosed volume of liquid.

17. The method of claim 14, further comprising:

monitoring temperature of liquid of the substantially enclosed volume of liquid and delivering the freezing agent as a function of temperature of the liquid.

18. The method of claim 14, further comprising:

imaging the prostate using the transrectal imaging probe; and monitoring a zone of frozen tissue of the prostate with the imaging.

19. A method of performing cryotherapy of a prostate, the method comprising:

spacing the prostate and a transrectal imaging probe with a volume of liquid therebetween;

delivering a freezing agent proximate the prostate to cause freezing of tissue thereof;

imaging the prostate using the transrectal imaging probe; and monitoring freezing of the tissue of the prostate with the imaging;

wherein the volume of liquid is disposed in at least one expandable enclosure.

20. The method of claim 19, further comprising:

regulating temperature of the volume of liquid.

21. The method of claim 19, further comprising:

recirculating liquid of the volume of liquid using a pump.

22. The method of claim 19, further comprising:

heating liquid of the volume of liquid using a liquid heater.

23. The method of claim 19, further comprising:

cooling liquid of the volume of liquid using a liquid cooler.

* * * * *

UNITED STATES PATENT AND TRADEMARK OFFICE
CERTIFICATE OF CORRECTION

PATENT NO. : 7,563,260 B2  
APPLICATION NO. : 11/207716  
DATED : July 21, 2009  
INVENTOR(S) : Willet F. Whitmore, III et al.

Page 1 of 1

It is certified that error appears in the above-identified patent and that said Letters Patent is hereby corrected as shown below:

Title Page

In Item (75) Inventors, replace "Willet F. Whitmore, Sarasota, FL (US);" with --Willet F. Whitmore III, Sarasota, FL (US);--.

In claim 9, Col. 11, line 4, replace "method .of" with --method of--.

In claim 11, Col. 11, line 13, replace "substantia11y" with --substantially--.

Signed and Sealed this

Fifteenth Day of September, 2009

David J. Kappos
*Director of the United States Patent and Trademark Office*